United States Patent
Carinci et al.

(10) Patent No.: US 10,996,307 B2
(45) Date of Patent: May 4, 2021

(54) MAGNETIC RESONANCE APPARATUS AND OPERATING METHOD WITH ADJUSTMENT OF THE EXCITATION ANGLE DEPENDENT ON DATA ACQUISITION FIELD OF VIEW

(71) Applicant: Siemens Healthcare GmbH, Erlangen (DE)

(72) Inventors: Flavio Carinci, Wuerenlingen (CH); George William Ferguson, Erlangen (DE); Michael Koehler, Nuremberg (DE); Dieter Ritter, Fuerth (DE); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 9 days.

(21) Appl. No.: 16/438,967

(22) Filed: Jun. 12, 2019

(65) Prior Publication Data

US 2019/0377052 A1  Dec. 12, 2019

(30) Foreign Application Priority Data

Jun. 12, 2018 (DE) .......................... 102018209352.0

(51) Int. Cl.
```
G01R 33/58    (2006.01)
G01R 33/561   (2006.01)
G01R 33/483   (2006.01)
G01R 33/32    (2006.01)
A61B 5/055    (2006.01)
```

(52) U.S. Cl.
CPC ............ *G01R 33/583* (2013.01); *A61B 5/055* (2013.01); *G01R 33/32* (2013.01); *G01R 33/4831* (2013.01); *G01R 33/5617* (2013.01)

(58) Field of Classification Search
CPC .............. G01R 33/583; G01R 33/5617; G01R 33/4831; G01R 33/32; G01R 33/283; G01R 33/5659; G01R 33/543; A61B 5/055
See application file for complete search history.

(56) References Cited

U.S. PATENT DOCUMENTS

2002/0186870 A1* 12/2002 Ma .................... G01R 33/3415
                                                          382/131
2007/0108976 A1    5/2007 Morich et al.
2016/0282438 A1    9/2016 Sun et al.

OTHER PUBLICATIONS

German action dated Jul. 6, 2020, Application No. 10 2018 209 352.0 (with translation).

* cited by examiner

*Primary Examiner* — Susan S Lee
(74) *Attorney, Agent, or Firm* — Schiff Hardin LLP

(57) ABSTRACT

In a magnetic resonance tomography (MRT) apparatus and operating method, a field of view for imaging a target object is acquired. A relative position of this field of view in relation to a receiving space of the MRT scanner, in which the target object is received, is then automatically determined. A radio-frequency (RF) pulse to be used by the MRT scanner for imaging the target object is then automatically adjusted depending on this relative position. An excitation angle produced in the field of view by the RF pulse is changed compared to the use of the corresponding unadjusted RF pulse.

11 Claims, 3 Drawing Sheets

MAGNETIC RESONANCE APPARATUS AND OPERATING METHOD WITH ADJUSTMENT OF THE EXCITATION ANGLE DEPENDENT ON DATA ACQUISITION FIELD OF VIEW

BACKGROUND OF THE INVENTION

Field of the Invention

The present invention concerns a method for operating a magnetic resonance tomography (MRT) apparatus, and a non-transitory, computer-readable data storage medium encoded with programming code that implement such a method.

Description of the Prior Art

Magnetic resonance tomography (MR, MRT, MRI) is a known technique for imaging an examination object or a target object. The target object can be almost any object, but a main field of application of MRT is the examination or imaging of biological tissue, for instance in a patient. Advantageously, no surgical intervention is necessary to image inner regions of the respective target object or patient. In the present case, imaging the target object means acquiring raw data from at least one slice or a section of the target object, with image data then being subsequently reconstructed from the raw data of known methods.

With MRT, a spatial volume, in which the target object for imaging is situated, is penetrated by a basic magnetic field $B_0$ produced by a magnet of the scanner. Magnetic moments of nuclear spins in the target object are thereby oriented along the field lines of the $B_0$ field. A magnetic alternating field $B_1$ (radio-frequency (RF) field) is then applied substantially perpendicularly to the $B_0$ field, in order to deflect the orientation by a defined angle. To enable consistent and realistic imaging of the target object, an optimally homogeneous, in other words uniform, field strength or distribution of this $B_1$ field inside the target object or inside the spatial volume available for images, must be produced by the basic field magnet of the scanner. With current MRT devices, the $B_1$ field has inhomogeneities, for example due to technical limitations and/or a coupling, in other words a feedback effect and/or influencing of the $B_1$ field, by the target object. The angle through which the magnetization or the corresponding magnetic moments are deflected or moved from the direction of the $B_0$ field by the $B_1$ field, called the excitation angle or a flip angle, depends on the local field strength of the $B_1$ field. Inhomogeneities of the $B_1$ field therefore lead to correspondingly location-dependent (spatially dependent), different or varying excitation angles, and this in turn impairs the imaging or image quality of the reconstructed image of the target object.

SUMMARY OF THE INVENTION

An object of the present invention is to improve the image quality of the image of the target object produced by an MRT apparatus.

The inventive method operates or controls an MRT apparatus that has a magnetic resonance scanner that has a receiving space for receiving a target object for imaging. The receiving space is therefore the spatial volume, from raw MR data can be recorded or acquired by the MRT scanner. The inventive method includes acquiring a specification of a field of view to be used by the MRT scanner for imaging the target object, which specifies a section of the receiving space or of the target object arranged therein, from which measurement data (raw data) of the target object are acquired, for imaging the target object. The field of view (FoV) can be designated, for example, a particular slice or a particular volume section of the target object, particularly when the target object is in a specified constant spatial positional relationship to the MRT scanner in the receiving space. The field of view therefore ultimately corresponds to the size of the reconstructed image of the target object.

The field of view to be used, in other words to be imaged, can be specified, for example, by an operator of the MRT scanner. Acquisition of the specification of the field of view can means that an appropriate manual input into the control computer of the MRT apparatus is automatically detected. The specification for the field of view to be used can also be done automatically, for example, by corresponding data or control signals or the like being retrieved by the MRT computer from a data memory or the like. The field of view to be used thus can be determined or specified by an appropriate control program or a specified measuring sequence or the like.

In a further step of the inventive method, a relative position of the specified field of view in relation to the receiving space of the MRT scanner is automatically determined. In other words, the MRT scanner or a corresponding control computer automatically determines where in the receiving space the specified field of view is located, in other words from which section of the receiving space image data are to be acquired for imaging the target object. A specified reference point, for example a center point (isocenter) of the receiving space, or a support on which the target object is located in the receiving space, can be specified and used for this purpose. The relative position can be determined one-dimensionally, two-dimensionally or three-dimensionally according to requirements. Therefore, a spacing between the specified field of view and the center or reference point of the receiving space or, correspondingly, a spacing of the specified field of view from an edge of the receiving space, can be automatically determined. For this purpose, spatial coordinates of the specified field of view can be compared or matched with a specified spatial model of the MRT scanner.

In a further method step of the inventive method, at least one RF pulse to be used by the MRT scanner for requiring raw data from the target object in the section is then automatically adjusted depending on the determined relative position of the specified field of view. At least one excitation angle or flip angle produced in the field of view or in a corresponding region of the target object is accordingly changed in the method with respect to the unadjusted RF pulse that existed before the adjustment or change of the at least one RF pulse. In other words, the RF pulse is modified in order to adjust the resulting excitation angle to the respective position or spatial position of the field of view in the receiving space.

This inventive method is particularly advantageous since the $B_1$ field strength produced by conventional MRT scanners in an edge region of the respective receiving space usually has a different value than, for instance, in a center or center point of the respective receiving space. The $B_1$ field strength is precisely the magnetic field strength of the RF pulse adjusted in the present method. The adjusted RF pulse therefore forms or produces precisely the $B_1$ field in the specified field of view. Because the RF pulse is adjusted depending on the local or spatial relative position of the respective field of view, in other words, measuring or acquisition region, a spatial inhomogeneity of the respective $B_1$ field, which usually occurs in conventional MRT scanners, can therefore be effectively compensated. This in turn leads to improved image quality of the reconstructed MRT images of the target object. For example, gradations or shading ($B_1$ shading), which are often seen even inside a truly homogeneous tissue region of the target object in MRT images produced by conventional MRT scanners, can be compensated or avoided in this way. The inventive method therefore allows a more realistic image of the respective target object, and therefore ultimately a more reliable or accurate evaluation or diagnosis. The inventive method can be used for different acquisition methods, but particularly advantageously in spin echo-based acquisition methods or pulse sequences.

In an embodiment of the inventive method, the automatic adjustment of the at least one RF pulse changes its amplitude (level or power) with the duration of the RF pulse is maintained unchanged, i.e., is left with respect to the specification thereof in the data acquisition protocol, in other words with respect to the unadjusted RF pulse. The resulting excitation angle is dependent upon or is determined by the time integral of the respective RF pulse, which is the area under the RF pulse waveform, when the signal waveform thereof is plotted on a graph. Because in the present case the RF pulse, and therefore the excitation angle, is changed only by the adjustment of the amplitude of the RF pulse, the timing of a respective specified measuring or pulse sequence containing the adjusted RF pulse remains unchanged or unaffected. As a result, advantageously the inventive method can be combined particularly easily with existing or known MRT imaging methods and established measuring or pulse sequences.

In a further embodiment of the present invention, the automatic adjustment of the RF pulse changes the amplitude more, the closer the field of view is to an edge of the receiving space. The RF pulse can be decreased or reduced in amplitude and/or duration by a larger amount, the closer the field of view is arranged to the edge of the receiving space. In other words, the further removed the target object is from a center point of the receiving space the larger the change. An improved imaged quality can be achieved particularly reliably based on the knowledge that with conventional MRT devices, the effective $B_1$ field strength typically increases with increasing distance from the center point of the acquisition region, in other words as the edge of the acquisition region is progressively approached. In individual cases, the $B_1$ field strength can also decrease, toward the edge of the receiving space, and this can then be compensated by a corresponding increase in the amplitude and/or the duration of the RF pulse. A coordinate system can be specified, for example, which has its origin in a center point of the receiving space and/or the x-axis of which extends in or parallel to a plane of the patient support or a patient bed, on which the target object is situated in the receiving space for imaging. As a result, the position of the field of view in relation to the receiving space can then be determined and indicated particularly easily, and in a manner that can be comprehended particular easily and clearly by the operator, by a corresponding x coordinate.

In a further embodiment of the present invention, loading of the receiving space is automatically detected. An expected $B_1$ field strength is then automatically determined in the specified field of view depending on the detected loading. The RF pulse is then automatically adjusted depending on a difference between the expected $B_1$ field strength and a specified target field strength in order to align the excitation angle resulting with the expected $B_1$ field strength with a specified target excitation angle. This target excitation angle would be achieved or produced with the target field strength, in other words, if the unadjusted RF pulse were to be used and there were no inhomogeneities in the $B_1$ field strength in the receiving space. An appropriate specification or input by a user can be acquired or identified, for example by the MRT scanner, in order to detect the loading. The loading can indicate in particular properties of the target object, such as its spatial form, type, size, composition, body mass, water and/or body fat content, build, gender and/or the like.

Additionally or alternatively, the MRT scanner itself can have a sensor or detector that automatically detects the loading. This can be or include, for example, a camera having a corresponding data or image processing device, a weight sensor, a temperature sensor, or the like.

The respective loading, in other words the corresponding properties of the target object, can, as described, directly affect the $B_1$ field strength that is achievable or producible with a specified RF pulse waveform, in other words with a specified RF pulse. By detecting the loading, the RF pulse can be particularly accurately adjusted to the respective situation, in other words to the respective target object or the respective loading, so as to adapt or achieve the specified target excitation angle particularly accurately. Therefore, the image quality can be improved reliably and consistently.

To determine the expected $B_1$ field strength, for example a corresponding characteristic field or a corresponding tabular allocation can be specified between different loading levels or properties of the target object, and a respective effect on the $B_1$ field strength and can be automatically requested or retrieved and evaluated by the computerized MRT apparatus. Additionally or alternatively, a calculation model can be specified, in which the expected $B_1$ field strength is simulated using the unadjusted and the adjusted RF pulse respectively. The resulting excitation angle therefore can be simulated or determined on the basis of a model for different RF pulses, in other words for different adjustments or variations of the specified RF pulse. Therefore, the same target excitation angle can be consistently achieved over the entire acquisition region, independently of the respective relative position of the field of view.

In a further embodiment of the present invention, all pulses of a measurement or pulse sequence specified for respective imaging of the target object are changed in the same way as the above-mentioned RF pulse. In other words, all RF pulses used for imaging the target object are adjusted similarly or uniformly. This means that the same absolute or relative, for example percentage, change is applied to all pulses of the unadjusted specified pulse sequence. Therefore, all excitation angles used for imaging the target object are then adapted accordingly. This process can be implemented and achieved particularly quickly and easily.

In a further embodiment of the present invention, from a specified measurement or pulse sequence, only each excitation pulse of this specified pulse sequence is adjusted as the at least one RF pulse to be changed for imaging the target object. It is known that established pulse sequences, which are regularly applied in magnetic resonance tomography, include different types of pulses, such as excitation pulses, refocusing pulses, fat saturation pulses, inversion pulses and the like. Depending on the type or construction of the respective pulse sequence, a change in a pulse can also have effects on the response signal that occurs due to the radiation of a later pulse. If only the excitation pulse(s) is/are adjusted, undesirable effects of this kind can be minimized or avoided and an advantageous compromise can be achieved between effects of this kind and improved image quality. Furthermore, undesirable saturation of the target object, which could occur, for example, when all pulses of the sequence are amplified excessively, can be avoided.

In a further advantageous embodiment of the present invention, from a specified pulse sequence, only each refocusing pulse of this specified pulse sequence is adjusted as the at least one RF pulse to be changed for imaging the target object. In other words, all remaining pulses of the specified pulse sequence, which are not refocusing pulses, are applied unchanged according to the specified pulse sequence, and only the refocusing pulse(s) are adjusted such that an excitation angle modified accordingly with respect to the specified pulse sequence is produced. This method represents a particularly advantageous adaptation for spin echo or turbo spin echo sequences.

In a further embodiment of the present invention, from a specified measurement or pulse sequence, all RF pulses of this specified pulse sequence with the exception of all fat saturation pulses of this specified pulse sequence are adjusted as the at least one RF pulse to be changed for imaging the target object. In other words, each pulse of the specified pulse sequence, which is not a fat saturation pulse, is adjusted depending on the respective determined relative position of the field of view, while the fat saturation pulse(s) of the specified pulse sequence is/are left unchanged, in other words applied, for imaging the target object. This embodiment of the invention is particularly preferred since it has been found that the best results can be achieved thereby. At least in most cases or on average, the best image quality is thereby achieved.

Within the scope of the present invention, adaptation of the respective RF pulse should be understood as meaning, or be equated with, the adaptation or modification of the respective resulting excitation angle of the corresponding pulse. Depending on the embodiment of the MRT apparatus, its controller and/or user interface, the adaptation of the RF pulse can mean that the excitation angle is adjusted or adapted, and this is then automatically converted into a correspondingly adjusted RF pulse and/or a corresponding control signal. Due to the automatic adjustment of the RF pulse, a user or operator advantageously does not have to independently or manually adjust the RF pulse, i.e., its form, length and/or properties, with the present method. So the method can advantageously be applied or carried out particularly consistently and reliably and incorrect manual adjustment by a user can be ruled out or avoided as a source of error.

In a further embodiment of the present invention, the RF pulse is adjusted according to a specified function depending on the determined relative position of the field of view. The specified function is a quadratic function in each case dependent on a spatial variable, a polynomial function of more than the second degree, a step function or an exponential function or a mixture or combination of these functions or function types. The spatial variable preferably describes the spatial position of the respective field of view in relation to the receiving space, for example in relation to its center point or a different specified reference point and/or to a specified coordinate system of the receiving space. In other words, a functional correlation of the position or situation of the field of view is specified, according to which the RF pulse is changed. If, for example, a quadratic function is specified for this correlation or the corresponding dependency, this means, for example, that the RF pulse, in other words its amplitude, from a specified reference point, in particular from the center point of the receiving space, is quadratically changed, in particular increased, in other words is selected or adjusted to be greater, or increases, the further the field of view accordingly is from the reference or center point.

Which of these functions or functional correlations or dependencies is specified or used or selected in the individual case can depend, for example, on the respective individual MRT device, for instance depending on granularity, resolution of an adjustability or adaptability of the RF pulse or of the corresponding excitation angle. Similarly, the respectively used function can be specified, preferably automatically selected, for example depending on a form and/or a spatial characteristic of a material composition of the target object.

Different functions or dependencies can be specified for different MRT scanners or a number of these functions can be specified for an individual MRT scanner, and these are then automatically selected in the individual case, dependent on the situation. Similarly, a number of usable functions can be specified for a single MRT scanner in each case, from which the MRT scanner then automatically selects one to be used or applied in each case. Similarly, the respective user can select and/or adjust the function to be used according to his or her respective needs or requirements. The function or functions can each include one or more adjustable parameter (s), for example coefficients or exponents, which can be adjusted or specified by the respective user via a corresponding user interface, such as a corresponding input mask. Particularly advantageously, the inventive method can be thereby flexibly adjusted to the respective situation and to respective individual user wishes. Therefore, an optimum image quality in each case can be achieved particularly flexibly, in a large number of different situations or applications.

The present invention also encompasses a non-transitory, computer-readable data storage medium encoded with programming instructions (program code) that, when the storage medium is loaded into a control computer of an MRT apparatus, cause the control computer to operate the MRT apparatus so as to implement any or all embodiments of the method according to the invention as described above.

The present invention also encompasses an MRT apparatus having scanner with a receiving space for receiving or arranging a target object for imaging, and having a control computer configured to control the MRT apparatus according to at least one embodiment of the inventive method. For this purpose, the control computer or the inventive MRT device can include a processor device having a data carrier or data memory on which or in which program code is stored that encodes or represents the method steps of the corresponding inventive method. Therefore, the data carrier or data memory of the inventive MRT apparatus can be the inventive data storage device. The processor is configured to execute the program code in order to implement the inventive method. Accordingly, the inventive MRT apparatus has the properties and/or components or parts cited or described in connection with the inventive method. These can include, for example the user interface and/or the sensor or detection device for detecting the loading.

The attributes and embodiments of the inventive method described above and below, as well as the corresponding advantages, apply as well to the inventive MRT apparatus and the inventive data carrier. The invention also includes versions wherein the various embodiments may be used in combinations that differ from the combinations that are explicitly described herein.

DESCRIPTION OF THE PREFERRED EMBODIMENTS

Figure 1:
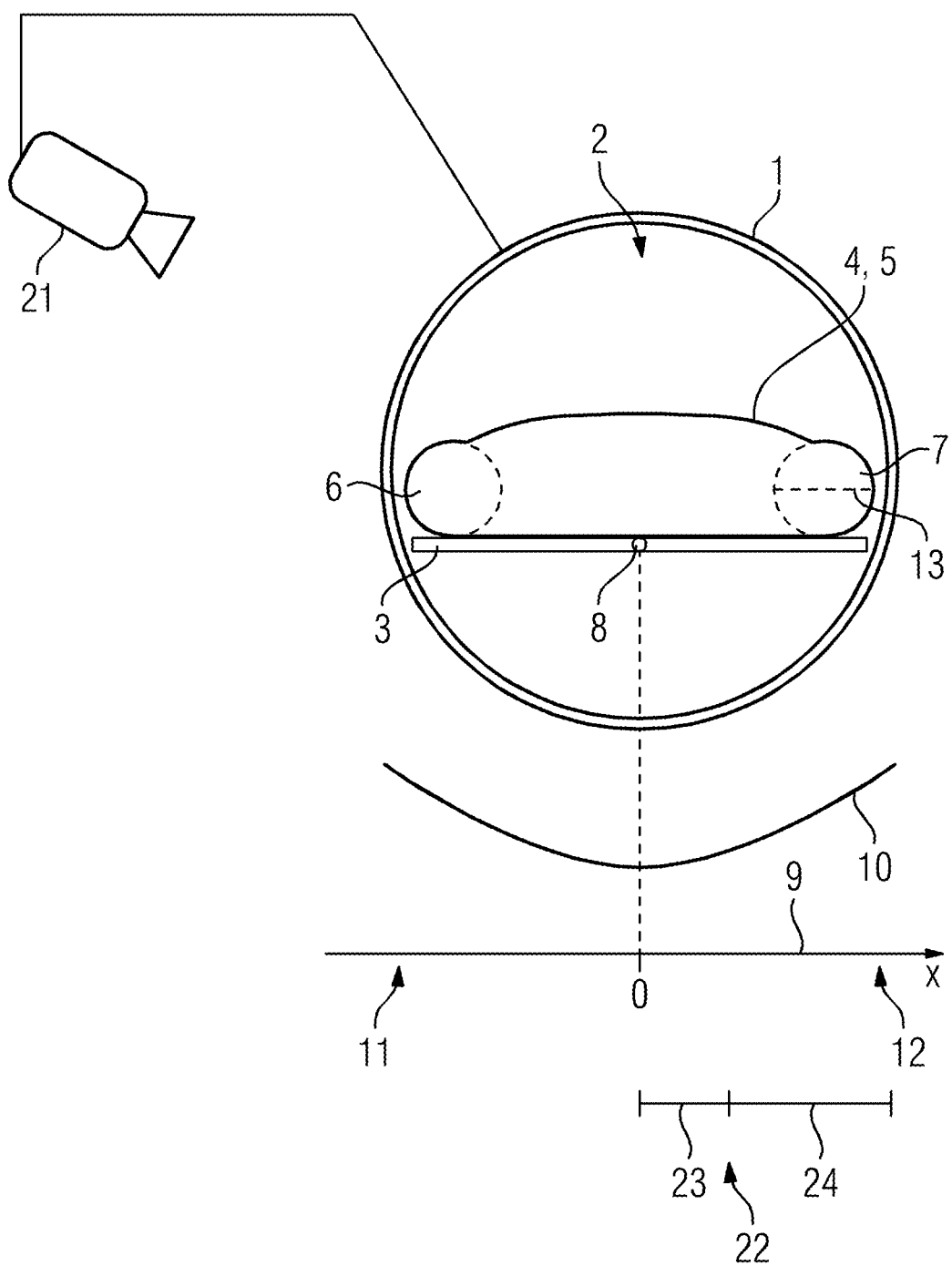
FIG. 1 schematically illustrates an inhomogeneity of the type that may occur in the execution of an MRT procedure.

The exemplary embodiments explained hereinafter are preferred embodiments of the invention. In the exemplary embodiments the described components of the embodiments are each individual features of the invention to be considered independently of each other, which each also develop the invention independently of each other and thereby can also be regarded as components of the invention, individually or in a combination different to that shown. Furthermore, the described embodiments can also be supplemented by further features of the invention already described.

Identical elements, those with the same function or mutually corresponding elements are each identified by the same reference characters in the figures.

FIG. 1 is a schematic diagram to illustrate an inhomogeneity in the case of an MRT procedure and to illustrate a method for operating an MRT scanner 1. The MRT scanner 1 is only schematically indicated as a ring here, which encloses a receiving space 2. In the present case a patient support 3 is arranged in the receiving space 2 as part of the MRT scanner 1. Here, the method can be in the form of a computer program, a computer program product or program code, which is stored on a data carrier that can be loaded into a control computer of the MRT scanner 1. The method is therefore carried out or applied by the computer program or the program code being executed by the control computer of the MRT scanner 1.

In the present case, a patient 4 is arranged on the patient support 3 in the receiving space 2 as a target object for imaging by the MRT scanner 1. The patient 4 has (schematically indicated) a torso 5 and a left arm 6 and a right arm 7. For imaging the patient 4, the receiving space 2 is penetrated by a static magnetic field $B_0$ and a magnetic alternating field $B_1$.

A reference point 8 is marked in a center point of the patient support 3. For further illustration, a spatial axis 9 is illustrated on which a spatial coordinate x is plotted, which indicates a position inside the receiving space 2 along the patient support 3 in relation to the reference point 8. An origin or zero point of the spatial axis 9 corresponds here to the location or the position of the reference point 8. An exemplary angular characteristic 10 is schematically illustrated or plotted in relation to the spatial axis 9 and the receiving space 2. This angular characteristic 10 illustrates a possible characteristic of a size of an excitation angle, which would result in the patient 4 when using an unmodified, specified measuring or pulse sequence for imaging the patient 4 over a width of the receiving space 2.

The pulse sequence is specified such that, under the assumption that ideal conditions exist throughout the receiving space 2, so an identical specified target excitation angle would be achieved. In reality, the MRT scanner 1 is subject onto technical limitations, and the patient 4 also can affect the angular characteristic 10, in other words an underlying field strength of the $B_1$ field. As a result, when using the specified pulse sequence, the angular characteristic 10 would be produced such that, for example, the specified target excitation angle would be achieved only in the region of the reference point 8, and in the direction of a left edge region 11 and in the direction of a right edge region 12 of the receiving space 2, an increasing (larger) excitation angle would occur. In other cases, dependent on the structure of the respective MRT system, an opposite angular characteristic may occur, which, without adjustment, reduces or decreases resulting excitation angles, from the reference point 8 to the edge regions 11, 12.

If, for example, the right arm 7 is to be imaged, then a schematically indicated field of view 13 can be specified for this imaging scan. As can be seen here with reference to the schematic illustration of the angular characteristic 10, a target excitation angle greater than the specified angle would then occur in the field of view 13.

Figure 2:
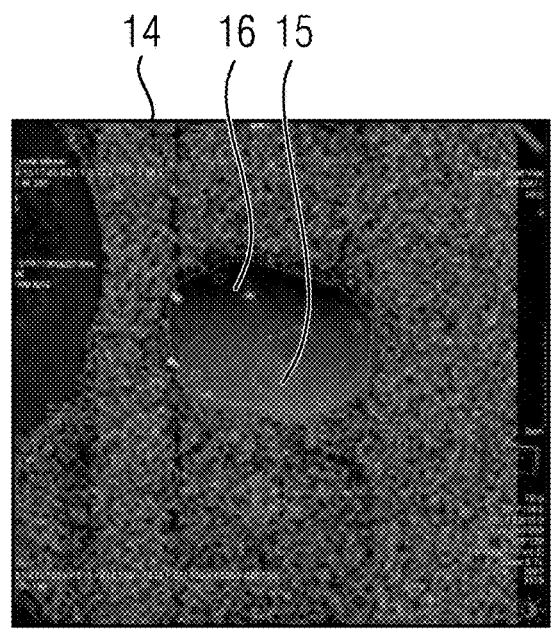
FIG. 2 shows a first MRT image having an undesirable brightness characteristic.

FIG. 2 shows a first MRT image 14, which was acquired by conventional operation of an MRT scanner, using the unmodified specified pulse sequence. Specifically, a $B_1$ field distribution in the region of an elbow is illustrated in the first MRT image 14. Due to the inhomogeneity of the B1 field in the receiving space 2, a brightness or intensity characteristic between a first section 15 and a second section 16 results, due to the spatial dependency of the excitation angle illustrated by the angular characteristic 10. This brightness or intensity characteristic, in other words a corresponding gradient, is an artifact, therefore does not depict an actual, real property of the imaged object.

Figure 3:
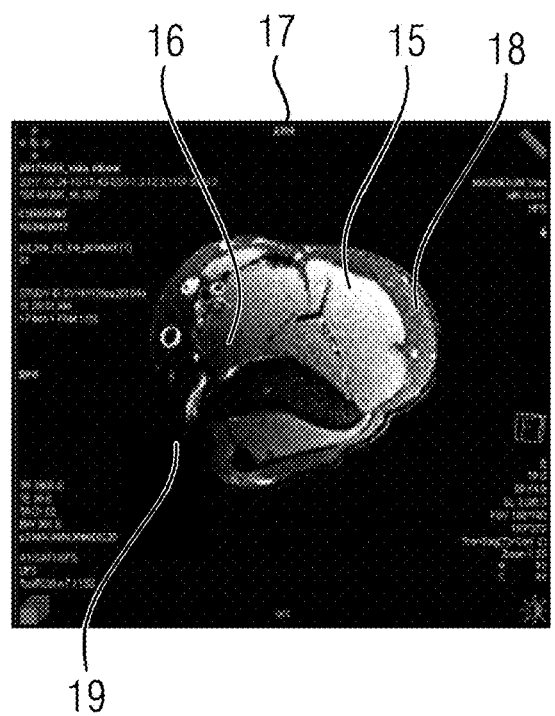
FIG. 3 shows a second MRT image having an undesirable brightness characteristic.

FIG. 3 shows a second MRT image 17, in which analogously to the first MRT image 14, a gradient between a first section 15 and a second section 16 of a real homogeneous tissue region is likewise illustrated. Furthermore, a third section 18 different from a fourth section 19 is depicted in the second MRT image 17, although these two sections 18, 19 have the same tissue type, ideally would be imaged identically therefore.

Figure 4:
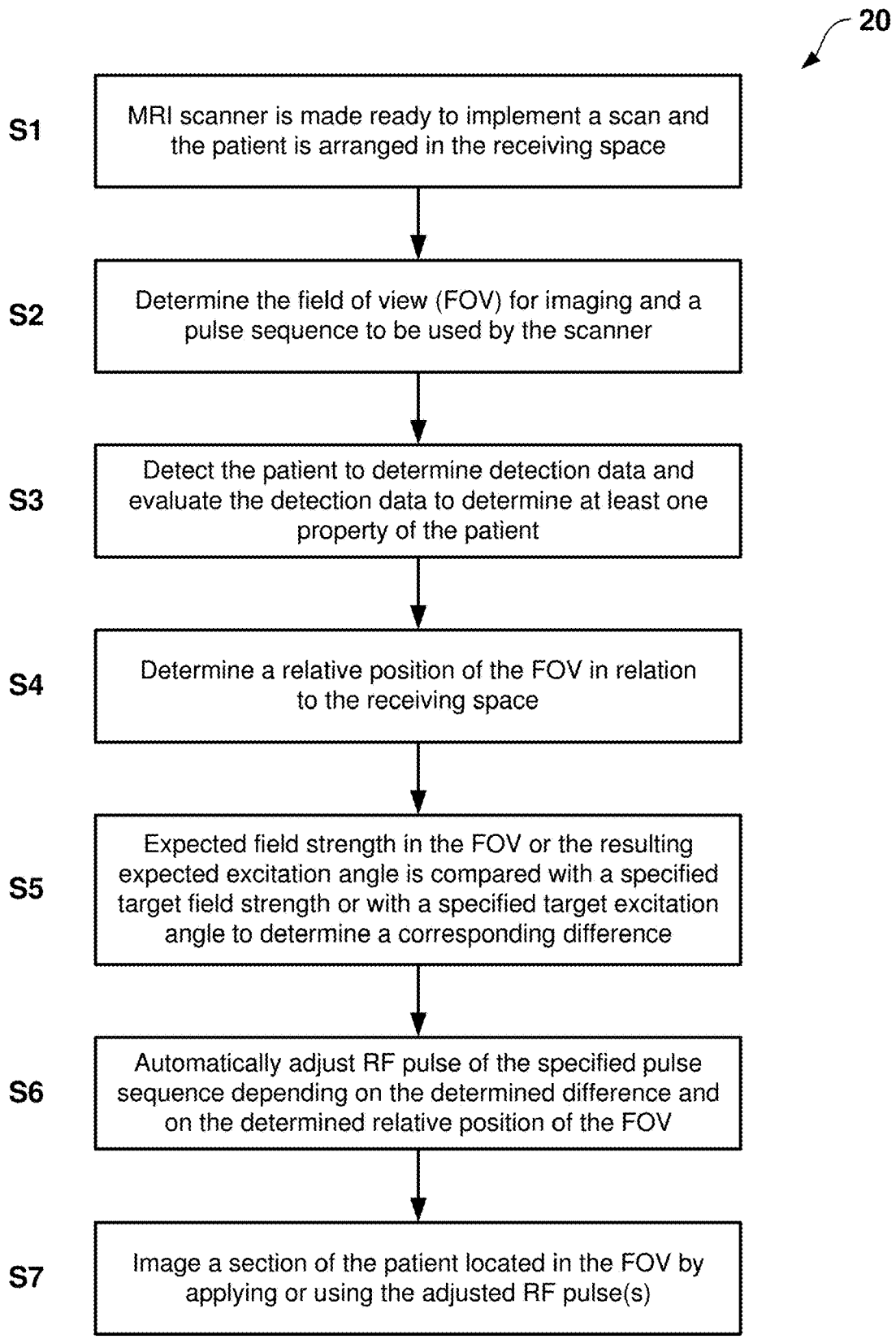
FIG. 4 is an exemplary flowchart of an embodiment of the method for operating an MRT apparatus according to the invention.

FIG. 4 schematically shows an exemplary flowchart 20 of a method for operating the MRT scanner 1 to achieve an improved image quality.

The method starts in method step S1 wherein the MRT scanner 1 is made ready implement a scan of the patient 4, and the patient 4 is arranged in the receiving space 2. This can include selecting or setting a data acquisition protocol in order to implement the scan, the control protocol including at least one RF pulse. The data acquisition protocol is provided to the control computer that operates the MR scanner 1.

The field of view 13 for imaging and a pulse sequence to be used by the MRT scanner 1 for imaging this field of view 13 or a corresponding section of the patient 4, are specified in method step S2.

Loading of the receiving space 21, here, the patient 4 therefore, is detected in a method step S3 by a detector 21 of the MRT scanner 1. Detection data supplied by the detector 21 are then automatically evaluated by the computer of the MRT scanner 1 in order to determine at least one property of the current loading, here, of the patient 4. For example, the build or body type of the patient 4 can be automatically determined by suitable image processing and execution of an object recognition algorithm. For example, a body fat percentage can be estimated. This can have a direct effect on the $B_1$ field strength that can be achieved with a specified RF pulse.

A relative position of the field of view 13 in relation to the receiving space 2, in particular in relation to the reference point 8, is determined in method step S4. A $B_1$ field strength expected in the region of the field of view 13 when using the specified pulse sequence, and a resulting excitation angle, is then determined by taking into account this determined relative position and the previously detected loading.

The expected $B_1$ field strength in the field of view 13 or the resulting expected excitation angle is compared with a specified $B_1$ target field strength or with a specified target excitation angle and a corresponding difference determined in method step S5.

An RF pulse of the specified pulse sequence is automatically adjusted by the control computer of the MRT scanner 1 depending on the determined difference—and therefore also depending on the determined relative position of the field of view 13 in relation to the reference point 8, in method step S6 in order to compensate the difference between the expected excitation angle and the specified target excitation angle. Therefore, in the present case a level or amplitude of at least one RF pulse of the specified pulse sequence is increased contrary to the angular characteristic 10.

The RF pulse(s) to be adjusted or the corresponding excitation or flip angles is/are therefore adapted according to the position of the field of view 13 or according to the position of a center of the field of view 13 in the receiving space 12 or on the spatial axis 9. After the adjustment or adaptation of the RF pulse(s), this does not produce the illustrated angular characteristic 10 in the field of view 13, and instead the specified target excitation angle is also achieved in the field of view 13, corresponding to a minimum of the angular characteristic 10 at x=0, therefore at the reference point 8.

Different adjustment or adaptation functions for scaling the RF pulse(s) or the corresponding excitation or flip angles are available for this purpose. Different target excitation angles can be specified for different RF pulses of the specified pulse sequence, so that, accordingly, different pulses of the specified pulse sequence can be scaled or adjusted in different ways in order to achieve the respective target excitation angle. For example, a target excitation angle of 90° can be specified for an excitation pulse of the specified pulse sequence. When using the unadjusted specified excitation pulse, however, this would only be achieved in the region of the reference point 8.

In the present case, the field of view 13 is located in a right-hand edge region 12 of the receiving space 2, however, so that when using the excitation pulse provided according to the specified pulse sequence, for example, an excitation angle of 100° would be achieved here. Depending on the specific MRT scanner 1 or depending on the situation or application, a quadratic function can be specified for adjusting or scaling the RF pulse or the corresponding excitation angle. The RF pulse is then scaled by a factor of $1/x^2$, with the determined position of the center of the field of view 13 on the spatial axis 9 being used for x.

A step function can likewise be specified. For this purpose, a boundary value 22 can be specified for x, which divides a region between the reference point 8 and an edge of the receiving space 2 into a first value range 23 and into a second value range 24. If the position x of the center of the field of view 13 is then in the first value range 23, then, for example, the specified pulse sequence can be used. If, on the other hand, the position x of the center of the field of view 13 is in the second value range 24, then the RF pulse to be adjusted in each case can be modified for instance by a specified, in particular constant, factor or offset.

A higher-order function, for example a fourth degree polynomial function, can likewise be specified for adjusting or scaling the respective RF pulse with or depending on the position of the field of view 13 relative to the reference point 8. An exponential function can likewise be specified for this, according to which the respective RF pulse is then modified for instance by a factor $|\exp(mx)|$. In this case m is a scaling or optimization factor, which can be adjusted or adapted for example by a respective user. The scaling factor m therefore provides an optimization option or an optimization criterion in order to further improve the image quality in the respective individual case, in other words, to actually be able to make an optimum adaptation.

A section of the patient 4 located in the field of view 13, in the present case corresponding to the right arm 7, is then imaged in a method step S7 by applying or using the adjusted RF pulse(s), in other words, by the correspondingly adjusted pulse sequence.

In summary, the described examples show how an automatic adaptation of an excitation flip angle can be implemented to improve the image quality. The described method can be applied particularly advantageously to TSE, SPACE, HASTE and SE sequences.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a magnetic resonance tomography (MRT) apparatus comprising an MRT data acquisition scanner having a receiving space for receiving a target object from which MRT data are to be acquired by executing an MRT data acquisition protocol, provided to a control computer of said MRT apparatus, said MRT data acquisition protocol comprising at least one radio-frequency (RF) pulse, said method comprising:
   providing said computer with a specification of a field of view that encompasses a portion of said receiving space from which said MRT data are to be acquired from said target object;
   in said computer, automatically determining a relative position of the field of view in relation to said receiving space of the MRT scanner; and
   in said computer, automatically adjusting said at least one RF pulse dependent on the determined relative position of the field of view, so as to change an excitation angle produced by said at least one RF pulse in said field of view, compared to an excitation angle produced by the original RF pulse in said MRT data acquisition protocol.

2. A method as claimed in claim 1 comprising changing an amplitude of said RF pulse while maintaining a duration of said RF pulse unchanged.

3. A method as claimed in claim 1 comprising making a larger change to said RF pulse as said specification of said field of view shows that said field of view is closer to an edge of said receiving space.

4. A method as claimed in claim 1 comprising:
   from said specification of said field of view, automatically determining a loading that exists in said receiving space;
   automatically determining an expected field strength of $B_1$ field produced by said RF pulse in said field of view, dependent on said loading; and
   changing said RF pulse dependent on a difference between the expected $B_1$ field strength and a specified target field strength in said MRT data acquisition protocol, so as to align said excitation angle resulting with the expected $B_1$ field strength with a specified target excitation angle produced by said target field strength.

5. A method as claimed in claim 1 wherein said MRT data acquisition protocol comprises a plurality of pulses, and changing all of said plurality of pulses in a same way as said at least one RF pulse.

6. A method as claimed in claim 1 wherein said MRT data acquisition protocol comprises a plurality of pulses, with only a subset of said plurality pulses being excitation pulses, and changing all excitation pulses in said subset in a same way as said at least one RF pulse.

7. A method as claimed in claim 1 wherein said MRT data acquisition protocol comprises a plurality of pulses, with only a subset of said plurality pulses being refocusing pulses, and changing all refocusing pulses in said subset in a same way as said at least one RF pulse.

8. A method as claimed in claim 1 wherein said MRT data acquisition protocol comprises a plurality of RF pulses, including fat saturation pulses, and changing all of said RF pulses, except said fat saturation pulses, in a same way as said at least one RF pulse is changed.

9. A method as claimed in claim 1 comprising changing said RF pulse according to a specified function selected from the group consisting of a quadratic function that is dependent on a spatial variable in said field of view, a polynomial function that is higher than a second degree, a step function, and an exponential function.

10. A magnetic resonance tomography (MRT) apparatus comprising:
an MRT data acquisition scanner comprising a receiving space in which a target object is received;
a control computer configured to operate the MRT data acquisition scanner in order to execute an MRT data acquisition protocol so as to acquire MRT data from the target object, said MRT data acquisition protocol comprising at least one RF pulse;
a detector that detects and provides said computer with a specification of a field of view that encompasses a portion of said receiving space from which said MRT data are to be acquired from said target object;
said computer being configured to automatically determine a relative position of the field of view in relation to said receiving space of the MRT scanner; and
said computer being configured to automatically adjust said at least one RF pulse dependent on the determined relative position of the field of view, so as to change an excitation angle produced by said at least one RF pulse in said field of view, compared to an excitation angle produced by the original RF pulse in said MRT data acquisition protocol.

11. A non-transitory, computer-readable data storage medium encoded with programming instructions, said storage medium being loaded into a control computer of a magnetic resonance tomography (MRT) apparatus that comprises an MRT data acquisition scanner having a receiving space in which a target object is received in order to acquire MRT data from the target object according to an MRT data acquisition protocol that comprises at least one RF pulse, said programming instructions causing said control computer to:
receive a specification of a field of view that encompasses a portion of said receiving space from which said MRT data are to be acquired from said target object;
determine a relative position of the field of view in relation to said receiving space of the MRT scanner; and
adjust said at least one RF pulse dependent on the determined relative position of the field of view, so as to change an excitation angle produced by said at least one RF pulse in said field of view, compared to an excitation angle produced by the original RF pulse in said MRT data acquisition protocol.

* * * * *